(12) United States Patent
Kadereit et al.

(10) Patent No.: US 8,222,240 B2
(45) Date of Patent: Jul. 17, 2012

(54) USE OF SUBSTITUTED CYCLOPROPANE ACID DERIVATIVES FOR PRODUCING DRUGS FOR USE IN THE TREATMENT OF METABOLIC SYNDROME

(75) Inventors: Dieter Kadereit, Offenbach (DE);
Siegfried Stengelin, Eppstein (DE);
Hubert Heuer, Schwabenheim (DE);
Harm Brummerhop, Frankfurt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 154 days.

(21) Appl. No.: 12/328,052

(22) Filed: Dec. 4, 2008

(65) Prior Publication Data

US 2009/0088474 A1 Apr. 2, 2009

Related U.S. Application Data

(60) Division of application No. 11/759,510, filed on Jun. 7, 2007, now abandoned, which is a continuation of application No. PCT/EP2005/012763, filed on Nov. 30, 2005.

(30) Foreign Application Priority Data

Dec. 14, 2004 (DE) .................. 10 2004 060 041
Aug. 19, 2005 (DE) .................. 10 2005 039 245

(51) Int. Cl.
*A61K 31/33* (2006.01)
(52) U.S. Cl. ..................................... 514/183
(58) Field of Classification Search .............. 514/183
See application file for complete search history.

(56) References Cited

U.S. PATENT DOCUMENTS

2004/0038941 A1* 2/2004 Zhu et al. ............ 514/79

FOREIGN PATENT DOCUMENTS

| WO | WO 02/066469 | 8/2002 |
| WO | WO 03/053352 | 7/2003 |
| WO | WO 03/053915 | 7/2003 |

OTHER PUBLICATIONS

Grandjean, D., et. al., Enzymatic Hydrolysis of Cyclopropanes. Total Synthesis of Optically Pure Dictyopterenes A and C'., Tetrahedron, vol. 47, No. 7, pp. 1215-1230 (1991).
Grundy, S., et. al., Drug Therapy of Metabolic Syndrome: Minimizing the Crisis of Polypharmacy, Nature Review Drug Discovery, vol. 5, pp. 295-309, (2006).

* cited by examiner

*Primary Examiner* — Brandon Fetterolf
*Assistant Examiner* — Christopher R Stone
(74) *Attorney, Agent, or Firm* — Brian R. Morrill; Scully, Scott, Murphy & Presser, P.C.

(57) ABSTRACT

The present invention comprises methods for reducing plasma lipids, plasma free fatty acids (FFA), plasma glycerol and triglycerides in a mammal through the administration of certain substituted cyclopropane acid derivatives of Formula 1:

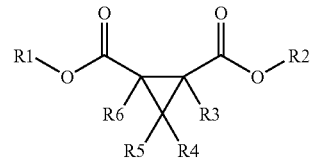

wherein R1-R6 are defined herein and pharmaceutical compositions comprising them.

1 Claim, No Drawings

USE OF SUBSTITUTED CYCLOPROPANE ACID DERIVATIVES FOR PRODUCING DRUGS FOR USE IN THE TREATMENT OF METABOLIC SYNDROME

CROSS REFERENCE TO RELATED APPLICATIONS

This is a divisional application of U.S. application Ser. No. 11/759,510 filed Jun. 7, 2007 which is a continuation of PCT/EP2005/012763 filed on Nov. 30, 2005 which claims the priority benefit of German Patent Application No. DE102004060041.4 filed on Dec. 14, 2004 and German Pat. Appln. No. DE102005039245.8 filed Aug. 19, 2005, all of which are incorporated herein by reference.

FIELD OF THE INVENTION

The invention relates to the use of certain substituted cyclopropane acid derivatives and of their physiologically tolerated salts for treating metabolic syndrome and related disorders.

BACKGROUND OF THE INVENTION

WO2002/066469 describes substituted cyclopropane acid derivatives as dopamine receptor ligands.

This invention is based on pursuit of the object of providing compounds which can be used for the treatment of the metabolic syndrome and which display, in particular, a therapeutically useful lipid-lowering effect. It was further intended, preferably, that they be suitable for the treatment of diabetic dyslipidemia. It was further intended, preferably, that a reduction in the free fatty acids (FFA), of glycerol and of triglycerides in the plasma be achieved.

SUMMARY OF THE INVENTION

The present invention relates to the use of compounds of the formula I

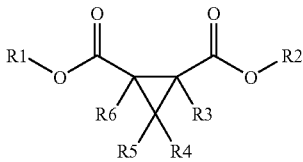

in which:
R1 is selected from H, $(C_1-C_{20})$-alkyl, $(C_2-C_{20})$-alkenyl, $(C_2-C_{20})$-alkynyl, aryl, and heterocycle, where the alkyl, alkenyl, alkynyl, aryl and heterocycle radicals may be substituted one or more times by a substituent selected from F, Cl, Br, I, $CF_3$, $NO_2$, $N_3$, CN, COOH, $COO(C_1-C_6)$alkyl, $CONH_2$, $CONH(C_1-C_6)$-alkyl, $CON[(C_1-C_6)$-alkyl$]_2$, cycloalkyl, $(C_1-C_{10})$-alkyl, $(C_2-C_6)$-alkenyl, $(C_2-C_6)$-alkynyl, $O-(C_1-C_6)$-alkyl $O-CO-(C_1-C_6)$-alkyl, $O-CO-(C_1-C_6)$-aryl, and $O-CO-(C_1-C_6)$-heterocycle; $PO_3H_2$, $P(O)(O$-alkyl$)_2$, $(C_1-C_6)$-alkylene-P(O)(O-alkyl$)_2$, $O-P(O)(OH)_2$, $O-P(O)(O$-alkyl$)_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, and $SO_2-N((CH_2)_n$-(heterocycle$)_2$ where n may be 0-6, and the aryl radical or heterocyclic radical may be substituted up to twice by a substituent selected from F, Cl, Br, OH, $CF_3$, $SF_5$, $NO_2$, CN, $OCF_3$, $O-(C_1-C_6)$-alkyl, $(C_1-C_6)$-alkyl, and $NH_2$; $C(NH)(NH_2)$, $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, NH-CO-aryl, NH-CO-heterocycle, NH-COO-aryl, NH-COO-heterocycle, $NH-CO-NH-(C_1-C_6)$-alkyl), NH-CO-NH-aryl, NH-CO-NH-heterocycle, $N[(C_1-C_6)$-alkyl]-CO-$(C_1-C_6)$-alkyl, $N[(C_1-C_6)$-alkyl]-COO-$(C_1-C_6)$-alkyl, $N[(C_1-C_6)$-alkyl]-CO-aryl, $N[(C_1-C_6)$-alkyl]-CO-heterocycle, $N[(C_1-C_6)$-alkyl]-COO-aryl, $N[(C_1-C_6)$-alkyl]-COO-heterocycle, $N[(C_1-C_6)$-alkyl]-CO-NH-$(C_1-C_6)$-alkyl), $N[(C_1-C_6)$-alkyl]-CO-NH-aryl, $N[(C_1-C_6)$-alkyl]-CO-NH-heterocycle, $N[(C_1-C_6)$-alkyl]-CO-N$((C_1-C_6)$-alkyl$)_2$, $N[(C_1-C_6)$-alkyl]-CO-N$((C_1-C_6)$-alkyl)-aryl, $N[(C_1-C_6)$-alkyl]-CO-N$((C_1-C_6)$-alkyl)-heterocycle, $N[(C_1-C_6)$-alkyl]-CO-N(Aryl$)_2$, $N[(C_1-C_6)$-alkyl]-CO-N (heterocycle$)_2$, N (aryl)-CO-$(C_1-C_6)$-alkyl, N(heterocycle)-CO-$(C_1-C_6)$-alkyl, N(aryl)-COO-$(C_1-C_6)$-alkyl, N(heterocycle)-COO-$(C_1-C_6)$-alkyl, N(aryl)-CO-aryl, N(heterocycle)-CO-aryl, N(aryl)-COO-aryl, N(heterocycle)-COO-aryl, N(aryl)-CO-NH-$(C_1-C_6)$-alkyl, N(heterocycle)-CO-NH-$(C_1-C_6)$-alkyl, N(aryl)-CO-NH-aryl, N(heterocycle)-CO-NH-aryl, N(aryl)-CO-N$((C_1-C_6)$-alkyl$)_2$, N(heterocycle)-CO-N$((C_1-C_6)$-alkyl$)_2$, N(aryl)-CO-N[$(C_1-C_6)$-alkyl]-aryl, N(heterocycle)-CO-N[$(C_1-C_6)$-alkyl]-aryl, N(aryl)-CO-N(aryl$)_2$, N(heterocycle)-CO-N(aryl$)_2$, Aryl, $O-(CH_2)_n$-aryl, and $O-(CH_2)_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SF_5$, $SO_2-CH_3$, COOH, COO-$(C_1-C_6)$-alkyl, and $CONH_2$;

R2 is selected from $(C_1-C_{20})$-alkyl, $(C_2-C_{20})$-alkenyl, $(C_2-C_{20})$-alkynyl, aryl, $(C_3-C_7)$-cycloalkyl, and heterocycle, where the alkyl, alkenyl, alkynyl, aryl, cycloalkyl and heterocycle radicals may be substituted one or more times by a substituent selected from F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)$alkyl$]_2$, cycloalkyl, $(C_1-C_{10})$-alkyl, $(C_2-C_6)$-alkenyl, $(C_2-C_6)$-alkynyl, $O-(C_1-C_6)$-alkyl $O-CO-(C_1-C_6)$-alkyl, $O-CO-(C_1-C_6)$-aryl, and $O-CO-(C_1-C_6)$-heterocycle; $PO_3H_2$, $P(O)(O$-alkyl$)_2$, $(C_1-C_6)$-alkylene-P(O)(O-alkyl$)_2$, $O-P(O)(OH)_2$, $O-P(O)(O$-alkyl$)_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, and $SO_2-N((CH_2)_n$-(heterocycle$)_2$ where n may be 0-6, and the aryl radical or heterocycle radical may be substituted up to twice by a substituent selected from F, Cl, Br, OH, $CF_3$, $SF_5$, $NO_2$, CN, $OCF_3$, $O-(C_1-C_6)$-alkyl, $(C_1-C_6)$-alkyl, and $NH_2$; $C(NH)(NH_2)$, $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, NH-CO-aryl, NH-CO-heterocycle, NH-COO-aryl, NH-COO-heterocycle, $NH-CO-NH-(C_1-C_6)$-alkyl), NH-CO-NH-aryl, NH-CO-NH-heterocycle, $N[(C_1-C_6)$-alkyl]-CO-$(C_1-C_6)$-alkyl, $N[(C_1-C_6)$-alkyl]-COO-$(C_1-C_6)$-alkyl, $N[(C_1-C_6)$-alkyl]-CO-aryl, $N[(C_1-C_6)$-alkyl]-CO-heterocycle, $N[(C_1-C_6)$-alkyl]-COO-aryl, $N[(C_1-C_6)$-alkyl]-COOheterocycle, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocycle, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocycle, N[($C_1$-$C_6$)-alkyl]-CO—N(aryl)$_2$, N[($C_1$-$C_6$)-alkyl]-CO—N(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl, N(heterocycle)-CO—NH—($C_1$-$C_6$)-alkyl, N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N[($C_1$-$C_6$)-alkyl]-aryl, N(heterocycle)-CO—N[($C_1$-$C_6$)-alkyl]-aryl, N(aryl)-CO—N(Aryl)$_2$, N(heterocycle)-CO—N(aryl)$_2$, Aryl, O—($CH_2$)$_n$-aryl, and O—($CH_2$)$_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, and $CONH_2$;

R3, R4, R5, and R6 are, independently of one another, selected from H, F, Cl, Br, I, OH, $CF_3$, $NO_2$, CN, $OCF_3$, ($C_1$-$C_6$)-alkyl, and O—($C_1$-$C_6$)-alkyl;

and the physiologically tolerated salts thereof for the treatment of metabolic syndrome.

Preference is given to the use of the compounds of the formula I in which:

R1 is H, or ($C_1$-$C_{20}$)-alkyl;

R2 is selected from ($C_1$-$C_{20}$)-alkyl, ($C_2$-$C_{20}$)-alkenyl, ($C_2$-$C_{20}$)-alkynyl, aryl, ($C_3$-$C_7$)-cycloalkyl, and heterocycle, where the alkyl, alkenyl, alkynyl, aryl, cycloalkyl and heterocycle radicals may be substituted one or more times by a substituent selected from F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle,
$PO_3H_2$, P(O)(O-alkyl)$_2$, ($C_1$-$C_6$)-alkylene-P(O)(O-alkyl)$_2$, O—P(O)(OH)$_2$, O—P(O)(O-alkyl)$_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N(($C_1$-$C_6$)-alkyl)($CH_2$)$_n$-aryl, $SO_2$—N(($C_1$-$C_6$)-alkyl)($CH_2$)$_n$-heterocycle, $SO_2$—N(($CH_2$)$_n$-aryl)$_2$, and $SO_2$—N(($CH_2$)$_n$-(heterocycle)$_2$ where n may be 0-6, and the aryl radical or heterocyclic radical may be substituted up to twice by a substituent selected from F, Cl, Br, OH, $CF_3$, $SF_5$, $NO_2$, CN, $OCF_3$, O—($C_1$-$C_6$)-alkyl, ($C_1$-$C_6$)-alkyl, and $NH_2$;
C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl), NH—CO—NH-aryl, NH—CO—NH-heterocycle, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocycle, N[($C_1$-$C_6$)-alkyl]-COO-aryl, N[($C_1$-$C_6$)-alkyl]-COO-heterocycle, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocycle, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocycle, N[($C_1$-$C_6$)-alkyl]-CO—N(aryl)$_2$, N[($C_1$-$C_6$)-alkyl]-CO—N(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl, N(heterocycle)-CO—NH—($C_1$-$C_6$)-alkyl, N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N[($C_1$-$C_6$)-alkyl]-aryl, N(heterocycle)-CO—N[($C_1$-$C_6$)-alkyl]-aryl, N(aryl)-CO—N(aryl)$_2$, N(heterocycle)-CO—N(aryl)$_2$, aryl, O—($CH_2$)$_n$-aryl, and O—($CH_2$)$_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, and $CONH_2$;

R3, R4, R5, and R6 are, independently of one another, selected from H, F, Cl, Br, I, OH, $CF_3$, $NO_2$, CN, $OCF_3$, ($C_1$-$C_6$)-alkyl, and O—($C_1$-$C_6$)-alkyl;

and the physiologically tolerated salts thereof.

DETAILED DESCRIPTION

Particular preference is given to the use of the compounds of the formula I in which:

R1 is H;

R2 is selected from ($C_1$-$C_{20}$)-alkyl, ($C_2$-$C_{20}$)-alkenyl, ($C_2$-$C_{20}$)-alkynyl, and ($C_3$-$C_7$)-cycloalkyl, where the alkyl, alkenyl, alkynyl and cycloalkyl radicals may be substituted one or more times by a substituent selected from F, Cl, Br, I, $CF_3$, $NO_2$, $N_3$, CN, COOH, COO($C_1$-$C_6$)alkyl, $CONH_2$, CONH ($C_1$-$C_6$)alkyl, CON[($C_1$-$C_6$)alkyl]$_2$, ($C_3$-$C_7$)-cycloalkyl, ($C_1$-$C_{10}$)-alkyl, ($C_2$-$C_6$)-alkenyl, ($C_2$-$C_6$)-alkynyl, O—($C_1$-$C_6$)-alkyl, O—CO—($C_1$-$C_6$)-alkyl, and O—CO—($C_1$-$C_6$)-aryl, $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—COO-aryl, NH—CO—NH—($C_1$-$C_6$)-alkyl), NH—CO—NH-aryl, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-COO-aryl, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(aryl)$_2$, N(aryl)-CO—($C_1$-$C_6$)-alkyl, N(aryl)-COO—($C_1$-$C_6$)-alkyl, N(aryl)-CO-aryl, N(aryl)-CO—NH—($C_1$-$C_6$)-alkyl N(aryl)-CO—NH-aryl, N(aryl)-CO—N(($C_1$-$C_6$)-alkyl)$_2$, N(aryl)-CO—N[($C_1$-$C_6$)-alkyl]-aryl, N(aryl)-CO—N(aryl)$_2$, aryl, and O—($CH_2$)$_n$-aryl;

R3, R4, R5, and R6 are independently selected from the group consisting of H, F, Cl, Br, I, OH, $CF_3$, $NO_2$, CN, $OCF_3$, ($C_1$-$C_6$)-alkyl, and O—($C_1$-$C_6$)-alkyl;

and the pharmaceutically acceptable salts thereof.

Very particular preference is given to the use of the compounds of the formula I in which:

R1 is H;

R2 is selected from ($C_1$-$C_{10}$)-alkyl, ($C_2$-$C_{10}$)-alkenyl, ($C_2$-$C_{10}$)-alkynyl, where the alkyl, alkenyl and alkynyl radicals may be substituted one or more times by F, Cl, Br, $CF_3$, $NO_2$, CN, COOH, COO($C_1$-$C_6$)alkyl, ($C_3$-$C_7$)-cycloalkyl, ($C_1$-$C_{10}$)-alkyl, ($C_2$-$C_6$)-alkenyl, ($C_2$-$C_6$)-alkynyl, O—($C_1$-$C_6$)-alkyl, O—CO—($C_1$-$C_6$)-alkyl, and O—CO—($C_1$-$C_6$)-aryl;

R3, R4, R5, and R6 are, independently of one another, selected from H, F, and ($C_1$-$C_4$)-alkyl;

and the pharmaceutically acceptable salts thereof.

The invention includes the use of the compounds of the formula I in the form of their racemates, racemic mixtures and pure enantiomers, and to their diastereomers and mixtures thereof.

If radicals or substituents may occur more than once in the compounds of the formula I, then they may all independently of one another have the stated meanings and be identical or different.

As used herein, 'alkyl radical' means a straight-chain or branched hydrocarbon chain having one or more carbon atoms, such as, for example, methyl, ethyl, propyl, butyl, hexyl, isopropyl, isobutyl, neopentyl, tert-butyl, and hexyl. The alkyl radicals may be substituted one or more times by suitable substituent groups such as, for example, F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, aryl, heterocycle, O—($C_1$-$C_6$)-alkyl, O—COO—($C_1$-$C_6$)-alkyl, O—CO—($C_1$-$C_6$)-alkyl, O—CO—($C_1$-$C_6$)-aryl, O—CO—($C_1$-$C_6$)-heterocycle, $PO_3H_2$, P(O)(O-alkyl)$_2$, ($C_1$-$C_6$)-alkylene-P(O)(O-alkyl)$_2$, O—P(O)(OH)$_2$, O—P(O)(O-alkyl)$_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N[(($C_1$-$C_6$)-alkyl)$(CH_2)_n$-aryl], $SO_2$—N[(($C_1$-$C_6$)-alkyl)$(CH_2)_n$-heterocycle], $SO_2$—N($(CH_2)_n$-aryl)$_2$, and $SO_2$—N($(CH_2)_n$-(heterocycle))$_2$, where n may be 0-6 and the aryl or heterocycle radical may be substituted up to three times by a substituent selected from F, Cl, Br, OH, $CF_3$, $SF_5$, $NO_2$, CN, $OCF_3$, O—($C_1$-$C_6$)-alkyl, ($C_1$-$C_6$)-alkyl, and $NH_2$; as well as from C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl), NH—CO—NH-aryl, NH—CO—NH-heterocycle, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocycle, N[($C_1$-$C_6$)-alkyl]-COO-aryl, N[($C_1$-$C_6$)-alkyl]-COO-heterocycle, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocycle, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocycle, N[($C_1$-$C_6$)-alkyl]-CO—N(aryl)$_2$, N[($C_1$-$C_6$)-alkyl]-CO—N(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl, N(heterocycle)-CO—NH—($C_1$-$C_6$)-alkyl, N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N[($C_1$-$C_6$)-alkyl]-aryl, N(heterocycle)-CO—N[($C_1$-$C_6$)-alkyl]-aryl, N(aryl)-CO—N(aryl)$_2$, N(heterocycle)-CO—N(aryl)$_2$, aryl, O—$(CH_2)_n$-aryl, and O—$(CH_2)_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, and $CONH_2$.

'Alkenyl radical' means a straight-chain or branched hydrocarbon chain having two or more carbon atoms and one or more double bonds, such as, for example, vinyl, allyl, and pentenyl. The alkenyl radicals may be substituted one or more times by suitable groups such as, for example, F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkynyl, aryl, heterocycle, O—($C_1$-$C_6$)-alkyl O—CO—($C_1$-$C_6$)-alkyl, O—CO—($C_1$-$C_6$)-aryl, and O—CO—($C_1$-$C_6$)-heterocycle; $PO_3H_2$, P(O)(O-alkyl)$_2$, ($C_1$-$C_6$)-alkylene-P(O)(O-alkyl)$_2$, O—P(O)(OH)$_2$, O—P(O)(O-alkyl)$_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N(($C_1$-$C_6$)-alkyl)$(CH_2)_n$-aryl, $SO_2$—N(($C_1$-$C_6$)-alkyl)$(CH_2)_n$-heterocycle, $SO_2$—N($(CH_2)_n$-aryl)$_2$, and $SO_2$—N($(CH_2)_n$-(heterocycle))$_2$ where n may be 0-6, and the aryl radical or heterocycle radical may be substituted up to twice by a substituent selected from F, Cl, Br, OH, $CF_3$, $SF_5$, $NO_2$, CN, $OCF_3$, O—($C_1$-$C_6$)-alkyl, ($C_1$-$C_6$)-alkyl, $NH_2$; as well as from C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl), NH—CO—NH-aryl, NH—CO—NH-heterocycle, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocycle, N[($C_1$-$C_6$)-alkyl]-COO-aryl, N[($C_1$-$C_6$)-alkyl]-COO-heterocycle, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocycle, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocycle, N[($C_1$-$C_6$)-alkyl]-CO—N(aryl)$_2$, N[($C_1$-$C_6$)-alkyl]-CO—N(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl, N(heterocycle)-CO—NH—($C_1$-$C_6$)-alkyl, N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N[($C_1$-$C_6$)-alkyl]-aryl, N(heterocycle)-CO—N[($C_1$-$C_6$)-alkyl]-aryl, N(aryl)-CO—N(aryl)$_2$, N(heterocycle)-CO—N(aryl)$_2$, aryl, O—$(CH_2)_n$-aryl, and O—$(CH_2)_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, and $CONH_2$.

'Alkynyl radical' means a straight-chain or branched-chain hydrocarbon having two or more carbon atoms and one or more triple bonds, such as, for example, ethynyl, propynyl, hexynyl. The alkynyl radicals may be substituted one or more times by suitable groups such as, for example, F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_1$-$C_{10}$)-alkyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, P(O)(O-alkyl)$_2$, ($C_1$-$C_6$)-alkylene-P(O)(O-alkyl)$_2$, O—P(O)(OH)$_2$, O—P(O)(O-alkyl)$_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, and $SO_2-N((CH_2)_n$-(heterocycle)$_2$ where n may be 0-6, and the aryl radical or heterocyclic radical may be substituted up to twice by a substituent selected from F, Cl, Br, OH, $CF_3$, $SF_5$, $NO_2$, CN, $OCF_3$, $O-(C_1-C_6)$-alkyl, $(C_1-C_6)$-alkyl, and $NH_2$; as well as $C(NH)(NH_2)$, $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, NH—CO-aryl, NH—CO-heterocycle, NH—COO-aryl, NH—COO-heterocycle, $NH-CO-NH-(C_1-C_6)$-alkyl), NH—CO—NH-aryl, NH—CO—NH-heterocycle, $N[(C_1-C_6)$-alkyl]-CO—$(C_1-C_6)$-alkyl, $N[(C_1-C_6)$-alkyl]-COO—$(C_1-C_6)$-alkyl, $N[(C_1-C_6)$-alkyl]-CO-aryl, $N[(C_1-C_6)$-alkyl]-CO-heterocycle, $N[(C_1-C_6)$-alkyl]-COO-aryl, $N[(C_1-C_6)$-alkyl]-COO-heterocycle, $N[(C_1-C_6)$-alkyl]-CO—NH—$(C_1-C_6)$-alkyl), $N[(C_1-C_6)$-alkyl]-CO—NH-aryl, $N[(C_1-C_6)$-alkyl]-CO—NH-heterocycle, $N[(C_1-C_6)$-alkyl]-CO—$N((C_1-C_6)$-alkyl$)_2$, $N[(C_1-C_6)$-alkyl]-CO—$N((C_1-C_6)$-alkyl)-aryl, $N[(C_1-C_6)$-alkyl]-CO—$N((C_1-C_6)$-alkyl)-heterocycle, $N[(C_1-C_6)$-alkyl]-CO—N(aryl)$_2$, $N[(C_1-C_6)$-alkyl]-CO—N(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(aryl)-COO-aryl, N(heterocycle)-COO-aryl, N(aryl)-CO—NH—$(C_1-C_6)$-alkyl, N(heterocycle)-CO—NH—$(C_1-C_6)$-alkyl, N(aryl)-CO—NH-aryl, N(heterocycle)-CO—NH-aryl, N(aryl)-CO—$N((C_1-C_6)$-alkyl$)_2$, N(heterocycle)-CO—$N((C_1-C_6)$-alkyl$)_2$, N(aryl)-CO—$N[(C_1-C_6)$-alkyl]-aryl, N(heterocycle)-CO—$N[(C_1-C_6)$-alkyl]-aryl, N(aryl)-CO—N(aryl)$_2$, N(heterocycle)-CO—N(aryl)$_2$, aryl, $O-(CH_2)_n$-aryl, and $O-(CH_2)_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SF_5$, $SO_2-CH_3$, COOH, COO—$(C_1-C_6)$-alkyl, and $CONH_2$.

'Aryl radical' means a phenyl, naphthyl, biphenyl, tetrahydronaphthyl, alpha- or beta-tetralon-, indanyl or indan-1-onyl radical. The aryl radicals may be substituted one or more times by suitable groups such as, for example, F, Cl, Br, I, $CF_3$, $NO_2$, $SF_5$, $N_3$, CN, COOH, $COO(C_1-C_6)$alkyl, $CONH_2$, $CONH(C_1-C_6)$alkyl, $CON[(C_1-C_6)$alkyl]$_2$, cycloalkyl, $(C_1-C_{10})$-alkyl, $(C_2-C_6)$-alkenyl, $(C_2-C_6)$-alkynyl, $O-(C_1-C_6)$-alkyl $O-CO-(C_1-C_6)$-alkyl, $O-CO-(C_1-C_6)$-aryl, $O-CO-(C_1-C_6)$-heterocycle, $PO_3H_2$, $P(O)(O$-alkyl$)_2$, $(C_1-C_6)$-alkylene-$P(O)(O$-alkyl$)_2$, $O-P(O)(OH)_2$, $O-P(O)(O$-alkyl$)_2$, $SO_3H$, $SO_2-NH_2$, $SO_2NH(C_1-C_6)$-alkyl, $SO_2N[(C_1-C_6)$-alkyl]$_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, and $SO_2-N((CH_2)_n$-(heterocycle)$_2$ where n may be 0-6, and the aryl radical or heterocyclic radical may be substituted up to twice by a substituent selected from F, Cl, Br, OH, $CF_3$, $SF_5$, $NO_2$, CN, $OCF_3$, $O-(C_1-C_6)$-alkyl, $(C_1-C_6)$-alkyl, and $NH_2$; as well as
  C(NH)(NH$_2$), $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, NH—CO-aryl, NH—CO-heterocycle, NH—COO-aryl, NH—COO-heterocycle, $NH-CO-NH-(C_1-C_6)$-alkyl), NH—CO—NH-aryl, NH—CO—NH-heterocycle, $N[(C_1-C_6)$-alkyl]-CO—$(C_1-C_6)$-alkyl, $N[(C_1-C_6)$-alkyl]-COO—$(C_1-C_6)$-alkyl, $N[(C_1-C_6)$-alkyl]-CO-aryl, $N[(C_1-C_6)$-alkyl]-CO-heterocycle, $N[(C_1-C_6)$-alkyl]-COO-aryl, $N[(C_1-C_6)$-alkyl]-COO-heterocycle, $N[(C_1-C_6)$-alkyl]-CO—NH—$(C_1-C_6)$-alkyl), $N[(C_1-C_6)$-alkyl]-CO—NH-aryl, $N[(C_1-C_6)$-alkyl]-CO—NH-heterocycle, $N[(C_1-C_6)$-alkyl]-CO—$N((C_1-C_6)$-alkyl$)_2$, $N[(C_1-C_6)$-alkyl]-CO—$N((C_1-C_6)$-alkyl)-aryl, $N[(C_1-C_6)$-alkyl]-CO—$N((C_1-C_6)$-alkyl)-heterocycle, $N[(C_1-C_6)$-alkyl]-CO—N(aryl)$_2$, $N[(C_1-C_6)$-alkyl]-CO—N(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl, N(heterocycle)-CO—NH—$(C_1-C_6)$-alkyl, N(aryl)-CO—NH-aryl, N(heterocycle)-CO—NH-aryl, N(aryl)-CO—$N((C_1-C_6)$-alkyl$)_2$, N(heterocycle)-CO—$N((C_1-C_6)$-alkyl$)_2$, N(aryl)-CO—$N[(C_1-C_6)$-alkyl]-aryl, N(heterocycle)-CO—$N[(C_1-C_6)$-alkyl]-aryl, N(aryl)-CO—N(aryl)$_2$, N(heterocycle)-CO—N(aryl)$_2$, aryl, $O-(CH_2)_n$-aryl, and $O-(CH_2)_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SF_5$, $SO_2-CH_3$, COOH, COO—$(C_1-C_6)$-alkyl, and $CONH_2$.

'Cycloalkyl radical' means a ring system which comprises one or more rings and which is in saturated or partially unsaturated (having one or two double bonds) form, which is composed exclusively of carbon atoms, such as, for example, cyclopropyl, cyclopentyl, cyclopentenyl, cyclohexyl or adamantyl. The cycloalkyl radicals may be substituted one or more times by suitable groups such as, for example, F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)$alkyl]$_2$, cycloalkyl, $(C_1-C_{10})$-alkyl, $(C_2-C_6)$-alkenyl, $(C_2-C_6)$-alkynyl, $O-(C_1-C_6)$-alkyl $O-CO-(C_1-C_6)$-alkyl, $O-CO-(C_1-C_6)$-aryl, and $O-CO-(C_1-C_6)$-heterocycle; as well as $PO_3H_2$, $P(O)(O$-alkyl$)_2$, $(C_1-C_6)$-alkylene-$P(O)(O$-alkyl$)_2$, $O-P(O)(OH)_2$, $O-P(O)(O$-alkyl$)_2$, $SO_3H$, $SO_2-NH_2$, $SO_2NH(C_1-C_6)$-alkyl, $SO_2N[(C_1-C_6)$-alkyl]$_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, and $SO_2-N((CH_2)_n$-(heterocycle)$_2$ where n may be 0-6, and the aryl radical or heterocyclic radical may be substituted up to twice by a substituent selected from F, Cl, Br, OH, $CF_3$, $SF_5$, $NO_2$, CN, $OCF_3$, $O-(C_1-C_6)$-alkyl, $(C_1-C_6)$-alkyl, and $NH_2$; as well as
  C(NH)(NH$_2$), $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, NH—CO-aryl, NH—CO-heterocycle, NH—COO-aryl, NH—COO-heterocycle, $NH-CO-NH-(C_1-C_6)$-alkyl), NH—CO—NH-aryl, NH—CO—NH-heterocycle, $N[(C_1-C_6)$-alkyl]-CO—$(C_1-C_6)$-alkyl, $N[(C_1-C_6)$-alkyl]-COO—$(C_1-C_6)$-alkyl, $N[(C_1-C_6)$-alkyl]-CO-aryl, $N[(C_1-C_6)$-alkyl]-CO-heterocycle, $N[(C_1-C_6)$-alkyl]-COO-aryl, $N[(C_1-C_6)$-alkyl]-COO-heterocycle, $N[(C_1-C_6)$-alkyl]-CO—NH—$(C_1-C_6)$-alkyl), $N[(C_1-C_6)$-alkyl]-CO—NH-aryl, $N[(C_1-C_6)$-alkyl]-CO—NH-heterocycle, $N[(C_1-C_6)$-alkyl]-CO—$N((C_1-C_6)$-alkyl$)_2$, $N[(C_1-C_6)$-alkyl]-CO—$N((C_1-C_6)$-alkyl)-aryl, $N[(C_1-C_6)$-alkyl]-CO—$N((C_1-C_6)$-alkyl)-heterocycle, $N[(C_1-C_6)$-alkyl]-CO—N(aryl)$_2$, $N[(C_1-C_6)$-alkyl]-CO—N(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COOaryl, N(heterocycle)-COO-aryl, N(aryl)-CO—NH—($C_1$-$C_6$)-alkyl, N(heterocycle)-CO—NH—($C_1$-$C_6$)-alkyl, N(aryl)-CO—NH-aryl, N(heterocycle)-CO—NH-aryl, N(aryl)-CO—N(($C_1$-$C_6$)-alkyl)$_2$, N(heterocycle)-CO—N (($C_1$-$C_6$)-alkyl)$_2$, N(aryl)-CO—N[($C_1$-$C_6$)-alkyl]-aryl, N(heterocycle)-CO—N[($C_1$-$C_6$)-alkyl]-aryl, N(aryl)-CO—N(aryl)$_2$, N(heterocycle)-CO—N(aryl)$_2$, aryl, O—($CH_2$)$_n$-aryl, and O—($CH_2$)$_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, and $CONH_2$.

'Heterocycle', 'heterocycle' or 'heterocyclic radical' means rings and ring systems which, apart from carbon, also comprise heteroatoms such as, for example, nitrogen, oxygen or sulfur. This definition also includes ring systems in which the heterocycle or the heterocyclic radical is fused to one or more benzene nuclei. Suitable heterocycle or "heterocyclic radicals" are acridinyl, benzimidazolyl, benzofuryl, benzothienyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazol, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl, aziridinyl, azetininyl, azepanyl, azocanyl and xanthenyl.

'Pyridyl' stands for 2-, 3- and 4-pyridyl. 'Thienyl' stands both for 2- and 3-thienyl.

'Furyl' stands both for 2- and 3-furyl.

Also included are the corresponding N-oxides of these compounds, i.e. for example 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example, F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$) alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, and O—CO—($C_1$-$C_6$)-heterocycle; as well as $PO_3H_2$, P(O)(O-alkyl)$_2$, ($C_1$-$C_6$)-alkylene-P(O)(O-alkyl)$_2$, O—P(O)(OH)$_2$, O—P(O)(O-alkyl)$_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N (($CH_2$)$_n$-(heterocycle)$_2$ where n may be 0-6, and the aryl radical or heterocyclic radical may be substituted up to twice by a substituent selected from F, Cl, Br, OH, $CF_3$, $SF_5$, $NO_2$, CN, $OCF_3$, O—($C_1$-$C_6$)-alkyl, ($C_1$-$C_6$)-alkyl, and $NH_2$; as well as C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl), NH—CO—NH-aryl, NH—CO—NH-heterocycle, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocycle, N[($C_1$-$C_6$)-alkyl]-COO-aryl, N[($C_1$-$C_6$)-alkyl]-COO-heterocycle, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocycle, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocycle, N[($C_1$-$C_6$)-alkyl]-CO—N(aryl)$_2$, N[($C_1$-$C_6$)-alkyl]-CO—N(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl, N(heterocycle)-CO—NH—($C_1$-$C_6$)-alkyl, N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N[($C_1$-$C_6$)-alkyl]-aryl, N(heterocycle)-CO—N[($C_1$-$C_6$)-alkyl]-aryl, N(aryl)-CO—N(aryl)$_2$, N(heterocycle)-CO—N(aryl)$_2$, aryl, O—($CH_2$)$_n$-aryl, O—($CH_2$)$_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, $SF_5$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, and $CONH_2$.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the formula I are salts of inorganic acids such as hydrochloric, hydrobromic, phosphoric, metaphosphoric, nitric, sulfonic and sulfuric acids, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids, as well as L-ascorbic acid, salicylic acid, 1,2-benzisothiazol-3(2H)-one and 6-methyl-1,2,3-oxathiazin-4(3H)-one 2,2-dioxide. The chlorine salt is particularly preferably used for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise belong within the framework of the invention as useful intermediates for preparing or purifying pharmaceutically acceptable salts and/or for use in nontherapeutic, for example in vitro, applications.

The compounds of the formula I may also exist in various polymorphous forms, for example, as amorphous and crystalline polymorphous forms. All polymorphous forms of the compounds of the formula I belong within the framework of the invention and comprise a further aspect of the invention.

All references to "compound(s) of formula (I)" hereinafter refer to compound(s) of the formula (I) as described above, and their salts and solvates as described herein.

The compound(s) of the formula (I) may also be administered in combination with a further active ingredient.

The amount of a compound of formula (I) necessary to achieve the desired biological effect depends on a number of factors, e.g., the specific compound chosen, the intended use, the mode of administration and the clinical condition of the patient. The daily dose is generally in the range from 0.3 mg to 100 mg (typically from 3 mg to 50 mg) per day per kilogram of body weight, e.g. 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may comprise, for example, from 0.1 ng to 10 mg, typically from 1 ng to 10 mg, per milliliter. Single doses may comprise, for example, from 1 mg to 10 g of the active ingredient. Thus, ampoules for injections may comprise, for example, from 1 mg to 100 mg, and single-dose formulations which can be administered orally, such as, for example, capsules or tablets, may comprise, for example, from 1.0 to 1000 mg, typically from 10 to 600 mg. In the case of pharmaceutically acceptable salts, the aforementioned weight data refer to the weight of the benzothiazepine ion derived from the salt. For the prophylaxis or therapy of the abovementioned conditions, the compounds of formula (I) may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may comprise from 0.05% to 95% by weight of the active ingredient. Further pharmaceutically active substances may likewise be present, including further compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (e.g. subcutaneous, intramuscular, intradermal or intravenous) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable gastric juice-resistant coatings include cellulose acetate phthalate, polyvinal acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound. Pharmaceutical compositions suitable for rectal administration are preferably in the form of single-dose suppositories. These can be produced by mixing a compound of formula (I) with one or more conventional solid carriers, for example, cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example, from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are all antidiabetics mentioned in the Rote Liste 2004, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside, or with a compound as described in PCT/EP 2004/00269, PCT/EP 2003/05815, PCT/EP 2003/05814, PCT/EP 2003/05816, EP 0114531, U.S. Pat. No. 6,498,156.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 2000/11833, PCT/US 2000/11490, WO 03/020269.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with a bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an adenosine A1 agonist such as, for example, those described in EP 0912520 or PCT/EP06749.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]cyclohexylmethyl}amide, hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4- ylurea, hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethyl-amino]ethanol hydrochloride (WO 01/83451)), CB1 (cannabinoid receptor 1) receptor antagonists (e.g. rimonabant or the active ingredients mentioned in WO 02/28346, MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphtamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In a further embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

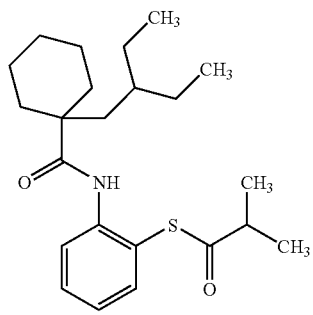
JTT-705

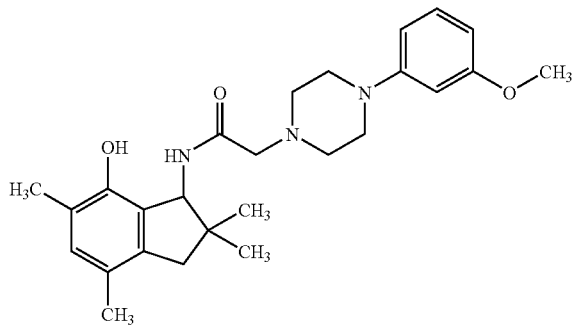
OPC-14117

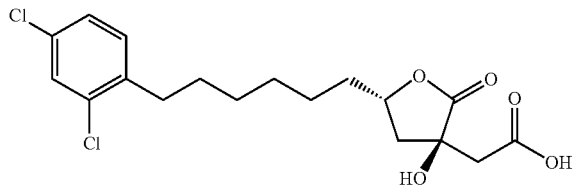
SB-204990

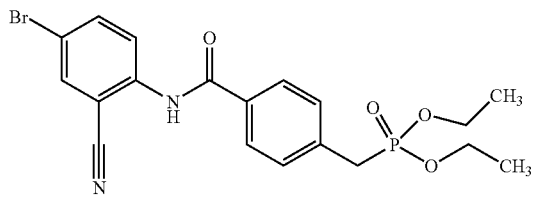
NO-1886

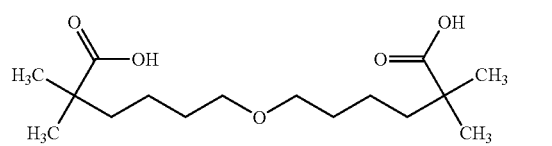
Cl-1027

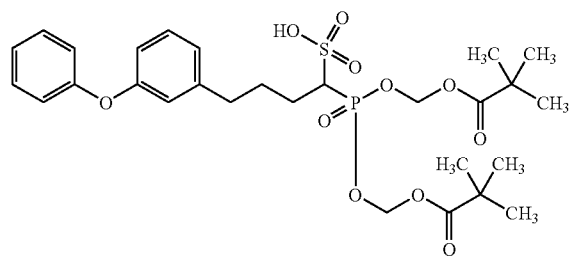
BMS-188494

-continued

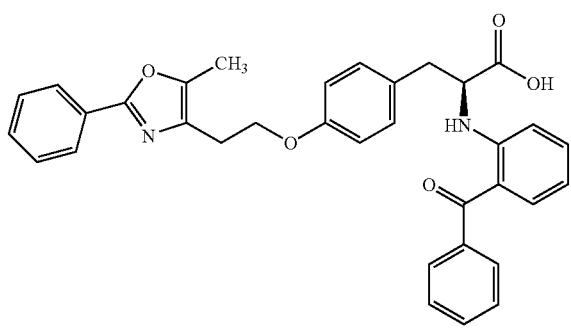

GI 262570

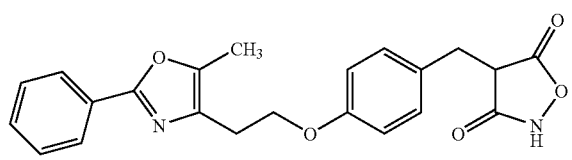

JTT-501

The examples detailed below serve to illustrate the invention but without restricting it, however.

| Example | Formula | Name | Salt |
|---------|---------|------|------|
| 1 | | 1R-Methoxycarbonyl-2R-hydroxycarbonyl-cyclopropane | Diethylmethylamine |
| 2 | | 1R-Methoxycarbonyl-2R-hydroxycarbonyl-cyclopropane | Quinidine |
| 3 | | 1R-Methoxycarbonyl-2R-hydroxycarbonyl-cyclopropane | |
| 4 | | Dimethyl cis-1,2-cyclopropanedicarboxylate | |
| 5 | | Dimethyl trans-1,2-cyclopropanedicarboxylate | |
| 6 | | Dimethyl 1-methyl-trans-cyclopropane-1,2-dicarboxylate | |

-continued

| Example | Formula | Name | Salt |
|---|---|---|---|
| 7 | | 1RS-Methoxycarbonyl-2RS-hydroxycarbonyl-cyclopropane | |
| 8 | | Diethyl trans-1,2-cyclopropanedicarboxylate | |
| 9 | | 1RS-Methoxycarbonyl-2RS-hydroxycarbonyl-3,3-dimethyl-cyclopropane | |
| 10 | | 1RS-Ethoxycarbonyl-2RS-hydroxycarbonyl-cyclopropane | |
| 11 | | 1RS-Propoxycarbonyl-2RS-hydroxycarbonyl-cyclopropane | |
| 12 | | 1RS-Butoxycarbonyl-2RS-hydroxycarbonyl-cyclopropane | |
| 13 | | 1RS-Pentoxycarbonyl-2RS-hydroxycarbonyl-cyclopropane | |
| 14 | | 1RS-iso-Propoxycarbonyl-2RS-hydroxycarbonyl-cyclopropane | |
| 15 | | 1RS-Cyclohexyl-methyloxycarbonyl-2RS-hydroxycarbonyl-cyclopropane | |
| 16 | | 1RS-isobutoxycarbonyl-2RS-hydroxycarbonyl-cyclopropane | |
| 17 | | 1RS-allyloxycarbonyl-2RS-hydroxycarbonyl-cyclopropane | |

| Example | Formula | Name | Salt |
|---|---|---|---|
| 18 | | 1RS-Propargyloxycarbonyl-2RS-hydroxycarbonyl-cyclopropane | |
| 19 | | 1RS-Butinyloxycarbonyl-2RS-hydroxycarbonyl-cyclopropane | |
| 20 | | 1RS-tertButoxycarbonyl-2RS-hydroxycarbonyl-3,3-dimethyl-cyclopropane | |
| 21 | | Diethyl 3,3-dimethyl-trans-1,2-cyclopropanedicarboxylate | |

The compounds of the formula I are suitable for the treatment of the metabolic syndrome (see Datamonitor November 2002, chapter 2, pages 19-32), for prediabetes treatment and for the prophylaxis of type 2 diabetes. They are particularly suitable for the treatment of diabetic dyslipidemia. Diabetic dyslipidemia is manifested by an elevation of plasma triglycerides, a reduction in HDL cholesterol and frequently in elevated LDL levels. Owing to the increased occurrence of small, dense LDL cholesterol particles of high atherogenic potency, diabetic dyslipidemia is a serious cardiovascular risk factor.

These compounds are further suitable for the treatment and/or prevention of 1. disorders of fatty acid metabolism and glucose utilization disorders,
disorders in which insulin resistance is involved,
hyperglycemia,
improvement in insulin resistance,
improvement in glucose tolerance,
protection of the pancreatic β cells
prevention of macro- and microvascular disorders
dyslipidemias and their sequelae such as, for example, atherosclerosis, coronary heart disease, cerebrovascular disorders etc.
obesity (excess weight), including abdominal obesity
thromboses, hypercoagulable and prothrombotic stages (arterial and venous)
high blood pressure
heart failure such as, for example, (but not restricted thereto), following myocardial infarction, hypertensive heart disease or cardiomyopathy 2. further disorders or conditions in which for example inflammatory reactions or cell differentiation are involved:
  atherosclerosis such as, for example (but not restricted thereto), coronary sclerosis including angina pectoris or myocardial infarction, stroke
  vascular restenosis or reocclusion
  chronic inflammatory bowel diseases such as, for example, Crohn's disease and ulcerative colitis
pancreatitis
other inflammatory conditions
retinopathy
adipose cell tumors
adipose cell carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lung, of the kidney and the urinary tract, of the genital tract, prostate carcinomas etc.
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions modulated by PPAR
eczemas and neurodermatitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal warts, viral warts such as, for example, molluscum contagiosum, leukoplakia
papular dermatoses such as, for example, lichen planus skin cancer such as, for example, basal-cell carcinomas, melanomas or cutaneous T-cell lymphomas localized benign epidermal tumors such as, for example, keratoderma, epidermal naevi chilblains high blood pressure syndrome X polycystic ovary syndrome (PCOS)

asthma osteoarthritis lupus erythematosus (LE) or inflammatory rheumatic disorders such as, for example, rheumatoid arthritis vasculitis wasting (cachexia)

gout ischemia/reperfusion syndrome acute respiratory distress syndrome (ARDS)

The compounds of the formula I can be formulated for example in the following preparations:

Example A

Soft gelatin capsules containing 100 mg of active ingredient per capsule:

|  | per capsule |
| --- | --- |
| active ingredient | 100 mg |
| triglyceride mixture fractionated from coconut fat | 400 mg |
| capsule contents | 500 mg |

Example B

Emulsion containing 60 mg of active ingredient per 5 ml:

|  | per 100 ml of emulsion |
| --- | --- |
| active ingredient | 1.2 g |
| neutral oil | q.s. |
| sodium carboxymethylcellulose | 0.6 g |
| polyoxyethylene stearate | q.s. |
| glycerol, pure | 0.2 to 2.0 g |
| flavoring | q.s. |
| water (deionized or distilled) | ad 100 ml |

Example C

Rectal drug form containing 40 mg of active ingredient per suppository:

|  | per suppository |
| --- | --- |
| active ingredient | 40 mg |
| suppository base | ad 2 g |

Example D

Tablets containing 40 mg of active ingredient per tablet:

|  | per tablet |
| --- | --- |
| lactose | 600 mg |
| corn starch | 300 mg |
| soluble starch | 20 mg |
| magnesium stearate | 40 mg |
|  | 1000 mg |

Example E

Coated tablets containing 50 mg of active ingredient per coated tablets:

|  | Per coated tablet |
| --- | --- |
| active ingredient | 50 mg |
| corn starch | 100 mg |
| lactose | 60 mg |
| Sec. calcium phosphate | 30 mg |
| soluble starch | 5 mg |
| magnesium stearate | 10 mg |
| colloidal silica | 5 mg |
|  | 260 mg |

Example F

The following formulations are suitable for producing the contents of hard gelatin capsules:

| a) active ingredient | 100 mg |
| --- | --- |
| corn starch | 300 mg |
|  | 400 mg |
| b) active ingredient | 140 mg |
| lactose | 180 mg |
| corn starch | 180 mg |
|  | 500 mg |

Example G

Drops can be produced using the following formulation (100 mg of active ingredient in 1 ml=20 drops):

| active ingredient | 10 g |
| --- | --- |
| methyl benzoate | 0.07 g |
| ethyl benzoate | 0.03 g |
| ethanol, 96% | 5 ml |
| demineralized water | ad 100 ml |

The activity of the compounds of the formula I was tested as follows:

Biological Test Model:

The effect was tested on the whole animal (mouse, rat, hamster or dog), after a fasting period (e.g. of about 16 hours the substance is administered (e.g. p.o., iv., i.p., s.c.) and, with or without additional stimulation of endogenous lipolysis (e.g. by a bolus injection of 2 mg/kg i.p. isoprenaline), the effect of the test substance on lipolysis was determined on the basis of the liberated free fatty acids (FFA), glycerol and triglycerides by obtaining a blood sample (e.g. by retroorbital blood sampling) e.g. 15 min, 30, 60, 120 etc minutes after p.o. administration, and analyzing by standard methods of clinical chemistry (e.g. L. Thomas: Labor und Diagnose, 2nd edition, Medizinische Verlagsgesellschaft, Marburg/L. 1984; ISBN 3-921320-10-9)). The inhibition of lipolysis by the inhibitors is analyzed by comparing with the rate of lipolysis in correspondingly treated control animals.

The product of Example 5 was administered in doses of from 0.3 to 30 mg/kg po, whereby the lipolysis was distinctly reduced, as it was possible to show from the reduction in free fatty acids (FFA), glycerol and triglycerides.

| FFA | | |
|---|---|---|
| Time | Control n = 15 | 3 mg/kg n = 6 |
| 0 | 0.47 | 0.47 |
| 15 | 0.60 | 0.17 |
| 30 | 0.62 | 0.13 |
| 60 | 0.62 | 0.11 |
| 120 | 0.69 | 0.25 |

| Glycerol | | |
|---|---|---|
| Time | Control n = 15 | 3 mg/kg n = 6 |
| 0 | 89 | 87 |
| 15 | 98 | 39 |
| 30 | 94 | 33 |
| 60 | 96 | 28 |
| 120 | 130 | 57 |

| Triglyceride | | |
|---|---|---|
| Time | Control n = 14 | 3 mg/kg n = 6 |
| 0 | 0.36 | 0.45 |
| 15 | 0.40 | 0.45 |
| 30 | 0.38 | 0.26 |
| 60 | 0.37 | 0.15 |
| 120 | 0.37 | 0.13 |

"n" stands for the number of animals. Wistar rats were tested.

The activity of the compounds of the formula I was also tested in the following assays:
in vitro functional assays with recombinant cells; function-testing assays were carried out by means of the FLIPR technique ("Fluorescence Imaging Plate Reader", Molecular Devices Corp.). For this purpose, agonist-induced changes in the intracellular concentration of $Ca^{2+}$ in recombinant HEK293 cells which express both the GPCR HM74A (niacin receptor) and the hybrid G-protein $G\square6qi4myr$ (see, for example, DE patent application 10033353) were determined.

For the investigations, cells were seeded into 96-well microtiter plates (60 000 cells/well) and allowed to grow overnight. The medium was removed and the cells were incubated in buffer which contained the fluorescent dye Fluo-4. After this loading with dye, the cells were washed, test substance was added, and changes in the intracellular $Ca^{2+}$ concentration were measured in the FLIPR apparatus. Results have been shown as percentage change relative to the control (0%: no test substance added; 100%: 1 µM reference agonist niacin added), used to calculate dose/activity plots and EC50 values determined.

TABLE 2

| Biological activity | |
|---|---|
| Example No. | EC50 (HM74a) µM |
| 1 | 0.07 |
| 2 | 0.13 |
| 3 | 0.19 |
| 4 | >30 |
| 5 | >30 |
| 6 | >30 |
| 7 | 0.63 |
| 8 | >30 |
| 9 | >30 |
| 10 | 1.48 |
| 11 | 2.16 |
| 12 | 0.67 |
| 13 | 1.61 |
| 14 | >30 |
| 15 | >30 |
| 16 | >30 |
| 17 | 2.83 |
| 18 | 1.51 |
| 19 | 1.63 |
| 20 | >30 |
| 21 | >30 |

The compounds of examples 1, 4, 5, 6, 8 and 21 were purchased from chemicals suppliers such as Fluka®, Aldrich® or Acros®. The compounds of examples 2 and 3 are disclosed in WO 2002/066469.

Synthesis of (1RS)-pentoxycarbonyl-(2RS)-hydroxycarbonylcyclopropane

Example 13

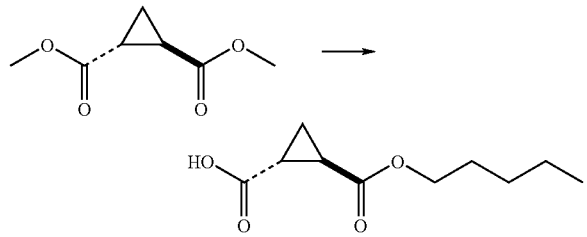

250 mg (1.58 mmol) of dimethyl trans-cyclopropane-1,2-dicarboxylate are dissolved in 5 ml of 1-pentanol, and 0.36 ml of a 5 molar aqueous NaOH solution is added. The reaction mixture is stirred at 25° C. for 5 days. Subsequently, 50 ml of water are added and the reaction mixture is extracted twice with 30 ml of ethyl acetate each time. The organic phase is discarded, and the aqueous phase is adjusted to pH=2 with 2 molar hydrochloric acid and extracted 3 times with ethyl acetate. The combined organic phase is dried over $MgSO_4$ and concentrated in a rotary evaporator.

220 mg (1.10 mmol) of 1 RS-pentoxycarbonyl-2RS-hydroxycarbonylcyclopropane are obtained as a colorless oil.

Examples 7, 9, 10, 11, 12, 14, 15, 16, 17, 18, 19 and 20 were synthesized in analogy to this general procedure starting from the appropriate dimethyl ester or diethyl ester.

What is claimed is:

1. A method for the treatment of diabetic dyslipidemia in a mammal, which comprises administering to said mammal a therapeutically effective amount of a compound of formula I,

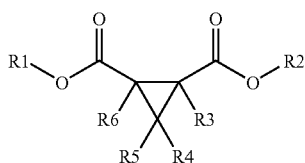

in which

R1 is selected from the group consisting of H, $(C_1-C_{20})$-alkyl, $(C_2-C_{20})$-alkenyl, $(C_2-C_{20})$-alkynyl, aryl, and heterocycle, where the alkyl, alkenyl, alkynyl, aryl and heterocycle groups may be substituted one or more times by a substituent selected from F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, cycloalkyl, $(C_1-C_{10})$-alkyl, $(C_2-C_6)$-alkenyl, $(C_2-C_6)$-alkynyl, O—$(C_1-C_6)$-alkyl O—CO—$(C_1-C_6)$-alkyl, O—CO—$(C_1-C_6)$-aryl, and O—CO—$(C_1-C_6)$-heterocycle; as well as from $PO_3H_2$, $P(O)(O$-alkyl$)_2$, $(C_1-C_6)$-alkylene-$P(O)(O$-alkyl$)_2$, O—$P(O)(OH)_2$, O—$P(O)(O$-alkyl$)_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle $SO_2$—$NH(CH_2)_n$-aryl, $SO_2$—$NH(CH_2)_n$-heterocycle, $SO_2$—$N((C_1-C_6)$-alkyl$)(CH_2)_n$-aryl, $SO_2$—N$((C_1-C_6)$-alkyl$)(CH_2)_n$-heterocycle, $SO_2$—$N((CH_2)_n$-aryl$)_2$, and $SO_2$—$N((CH_2)_n$-(heterocycle$)_2$ where n may be 0-6, and the aryl radical or heterocyclic radical may be substituted up to twice by a substituent selected from F, Cl, Br, OH, $CF_3$, $SF_5$, $NO_2$, CN, $OCF_3$, O—$(C_1-C_6)$-alkyl, $(C_1-C_6)$-alkyl, and $NH_2$; as well as from C(NH)($NH_2$), $NH_2$, NH—$(C_1-C_6)$-alkyl, $N((C_1-C_6)$-alkyl$)_2$, $NH(C_1-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, $N[(C_1-C_6)$-alkyl$]$-CO—$(C_1-C_6)$-alkyl, $N[(C_1-C_6)$-alkyl$]$-COO—$(C_1-C_6)$-alkyl, $N[(C_1-C_6)$-alkyl$]$-CO-aryl, $N[(C_1-C_6)$-alkyl$]$-CO-heterocycle, $N[(C_1-C_6)$-alkyl$]$-COO-aryl, $N[(C_1-C_6)$-alkyl$]$-COO-heterocycle, $N[(C_1-C_6)$-alkyl$]$-CO—NH—$(C_1-C_6)$-alkyl), $N[(C_1-C_6)$-alkyl$]$-CO—NH-aryl, $N[(C_1-C_6)$-alkyl$]$-CO—NH-heterocycle, $N[(C_1-C_6)$-alkyl$]$-CO—$N((C_1-C_6)$-alkyl$)_2$, $N[(C_1-C_6)$-alkyl$]$-CO—$N((C_1-C_6)$-alkyl$)$-aryl, $N[(C_1-C_6)$-alkyl$]$-CO—N$((C_1-C_6)$-alkyl$)$-heterocycle, $N[(C_1-C_6)$-alkyl$]$-CO—N(Aryl$)_2$, $N[(C_1-C_6)$-alkyl$]$-CO—N(heterocycle$)_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl, N(heterocycle)-CO—NH—$(C_1-C_6)$-alkyl, N(aryl)-CO—NH-aryl, N(heterocycle)-CO—NH-aryl, N(aryl)-CO—$N((C_1-C_6)$-alkyl$)_2$, N(heterocycle)-CO—$N((C_1-C_6)$-alkyl$)_2$, N(aryl)-CO—$N[(C_1-C_6)$-alkyl$]$-aryl, N(heterocycle)-CO—$N[(C_1-C_6)$-alkyl$]$-aryl, N(aryl)-CO—N(aryl$)_2$, N(heterocycle)-CO—N(aryl$)_2$, Aryl, O—$(CH_2)_n$-aryl, and O—$(CH_2)_n$-heterocycle, where n may be 0-6, where the aryl or heterocycle radical may be substituted one to 3 times by a substituent selected from F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SF_5$, $SO_2$—$CH_3$, COOH, COO—$(C_1-C_6)$-alkyl, and $CONH_2$;

R2 is selected from $(C_1-C_{20})$-alkyl, $(C_2-C_{20})$-alkenyl, $(C_2-C_{20})$-alkynyl, aryl, $(C_3-C_7)$-cycloalkyl, and heterocycle, where the alkyl, alkenyl, alkynyl, aryl, cycloalkyl and R3, R4, R5, and R6 are, independently of one another, selected from H, F, Cl, Br, I, OH, $CF_3$, $NO_2$, CN, $OCF_3$, $(C_1-C_6)$-alkyl, and O—$(C_1-C_6)$-alkyl, wherein the alkyl in $(C_1-C_6)$-alkyl and O—$(C_1-C_6)$-alkyl is unsubstituted; and the pharmaceutically acceptable salts thereof.

* * * * *